(12) United States Patent
Stephan

(10) Patent No.: US 10,835,414 B2
(45) Date of Patent: *Nov. 17, 2020

(54) THERAPEUTIC TREATMENT PAD

(71) Applicant: Scott Stephan, Ham Lake, MN (US)

(72) Inventor: Scott Stephan, Ham Lake, MN (US)

( * ) Notice: Subject to any disclaimer, the term of this patent is extended or adjusted under 35 U.S.C. 154(b) by 537 days.

This patent is subject to a terminal disclaimer.

(21) Appl. No.: 14/733,200

(22) Filed: Jun. 8, 2015

(65) Prior Publication Data

US 2016/0030237 A1 Feb. 4, 2016

Related U.S. Application Data

(62) Division of application No. 13/010,254, filed on Jan. 20, 2011, now Pat. No. 9,050,175.

(51) Int. Cl.
*A61F 7/02* (2006.01)
*A61F 7/00* (2006.01)

(52) U.S. Cl.
CPC .............. *A61F 7/02* (2013.01); *A61F 7/007* (2013.01); *A61F 2007/0054* (2013.01); *A61F 2007/0055* (2013.01); *A61F 2007/0071* (2013.01); *A61F 2007/0219* (2013.01); *A61F 2007/0239* (2013.01); *A61M 2202/02* (2013.01); *A61M 2202/0225* (2013.01)

(58) Field of Classification Search
CPC combination set(s) only.
See application file for complete search history.

(56) References Cited

U.S. PATENT DOCUMENTS

| | | | |
|---|---|---|---|
| 3,783,870 A | 1/1974 | Schachet | |
| 3,809,086 A | 5/1974 | Schachet et al. | |
| 3,809,087 A | 5/1974 | Lewis, Jr. | |
| 3,867,939 A * | 2/1975 | Moore | A61F 7/02 604/291 |
| 3,889,101 A * | 6/1975 | Woods | A61F 7/007 219/212 |
| 4,073,294 A | 2/1978 | Stanley et al. | |

(Continued)

FOREIGN PATENT DOCUMENTS

GB 2 307 180 A 5/1997

OTHER PUBLICATIONS

US 6,216,701 B1, 04/2001, Heaton et al. (withdrawn)

(Continued)

*Primary Examiner* — Joseph A Stoklosa
*Assistant Examiner* — Adam J Avigan
(74) *Attorney, Agent, or Firm* — Merchant & Gould P.C.

(57) ABSTRACT

A treatment pad for applying heat, cooling or an antiseptic fluid to a subject's body surface incorporates a heat transfer member or a wound treatment member that is adapted to be held in place by application of a vacuum pressure. The heat transfer member may comprise an electrical resistance wire arranged in a serpentine pattern within a housing or, alternatively, may comprise interconnected heat transmissive tubing through which either a heated or a cooled fluid may be made to pass. Alternatively, the pad may contain a gel that can be cooled in a refrigerator or heated in a microwave oven and held in place on the subject's body by application of a vacuum to the assembly. The wound treatment member may comprise a gaseous antiseptic delivery pad held in place on the patient's body by use of a vacuum.

6 Claims, 5 Drawing Sheets

(56) References Cited

U.S. PATENT DOCUMENTS

| | | |
|---|---|---|
| 4,114,620 A | 9/1978 | Moore et al. |
| 4,149,541 A | 4/1979 | Gammons et al. |
| 4,266,545 A | 5/1981 | Moss |
| 4,278,089 A | 7/1981 | Huck et al. |
| 4,392,860 A | 7/1983 | Huck et al. |
| 4,396,011 A | 8/1983 | Mack et al. |
| 4,569,674 A | 2/1986 | Phillips et al. |
| 4,578,060 A | 3/1986 | Huck et al. |
| 4,655,754 A | 4/1987 | Richmond et al. |
| 4,661,093 A | 4/1987 | Beck et al. |
| 4,713,052 A | 12/1987 | Beck et al. |
| 4,798,583 A | 1/1989 | Beck et al. |
| 4,826,494 A | 5/1989 | Richmond et al. |
| 4,923,444 A | 5/1990 | Daoud et al. |
| 4,936,834 A | 6/1990 | Beck et al. |
| 4,969,880 A | 11/1990 | Zamierowski |
| 5,100,395 A | 3/1992 | Rosenberg |
| 5,141,503 A | 8/1992 | Sewell, Jr. |
| 5,456,704 A | 10/1995 | Kilcullen |
| 5,549,584 A | 8/1996 | Gross |
| 5,636,643 A | 6/1997 | Argenta et al. |
| 5,645,081 A | 7/1997 | Argenta et al. |
| 5,800,483 A * | 9/1998 | Vought ............. A61F 7/00 128/849 |
| 5,817,145 A * | 10/1998 | Augustine ......... A61F 7/007 607/96 |
| 5,817,150 A | 10/1998 | Owens |
| D406,899 S | 3/1999 | Cottle |
| 5,944,703 A | 8/1999 | Dixon et al. |
| 5,966,763 A | 10/1999 | Thomas et al. |
| 6,000,403 A * | 12/1999 | Cantwell ........... A61M 35/006 128/888 |
| 6,024,731 A | 2/2000 | Seddon et al. |
| 6,135,116 A | 10/2000 | Vogel et al. |
| D434,150 S | 11/2000 | Tumey et al. |
| 6,142,982 A | 11/2000 | Hunt et al. |
| D439,341 S | 3/2001 | Tumey et al. |
| 6,261,276 B1 | 7/2001 | Reitsma |
| 6,345,623 B1 | 2/2002 | Heaton et al. |
| 6,458,109 B1 * | 10/2002 | Henley ............. A61M 1/0088 604/289 |
| 6,553,998 B2 | 4/2003 | Heaton et al. |
| 6,648,862 B2 | 11/2003 | Watson |
| 6,685,681 B2 | 2/2004 | Lockwood et al. |
| 6,695,823 B1 | 2/2004 | Lina et al. |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,767,334 B1 | 7/2004 | Randolph |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,856,821 B2 | 2/2005 | Johnson |
| 6,936,037 B2 | 8/2005 | Bubb et al. |
| 6,951,553 B2 | 10/2005 | Bubb et al. |
| 6,979,324 B2 | 12/2005 | Bybordi et al. |
| 6,994,702 B1 | 2/2006 | Johnson |
| 7,004,915 B2 | 2/2006 | Boynton et al. |
| 7,022,113 B2 | 4/2006 | Lockwood et al. |
| 7,060,795 B2 | 6/2006 | Quirk |
| 7,128,735 B2 | 10/2006 | Weston |
| 7,338,482 B2 | 3/2008 | Lockwood et al. |
| 7,485,112 B2 | 2/2009 | Karpowicz et al. |
| 7,534,927 B2 | 5/2009 | Lockwood et al. |
| 7,708,724 B2 | 5/2010 | Weston |
| 7,723,560 B2 | 5/2010 | Lockwood et al. |
| 7,776,028 B2 | 8/2010 | Miller et al. |
| 7,779,004 B1 | 9/2010 | Tumey |
| 7,846,141 B2 | 12/2010 | Weston |
| 7,927,318 B2 | 4/2011 | Risk, Jr. et al. |
| 7,947,033 B2 | 5/2011 | Ganapathy et al. |
| 8,025,650 B2 | 9/2011 | Anderson et al. |
| 8,062,272 B2 | 11/2011 | Weston |
| 8,100,887 B2 | 1/2012 | Weston et al. |
| 8,168,848 B2 | 5/2012 | Lockwood et al. |
| 8,444,611 B2 | 5/2013 | Sanders et al. |
| 8,992,492 B2 | 3/2015 | Anderson et al. |
| 2003/0093041 A1 | 5/2003 | Risk, Jr. et al. |
| 2003/0212357 A1 * | 11/2003 | Pace ............. A61F 13/0203 602/41 |
| 2007/0161938 A1 * | 7/2007 | Aali ............. A61F 15/002 602/56 |
| 2007/0193588 A1 * | 8/2007 | Baumann ........ A61F 7/02 128/849 |
| 2009/0228082 A1 | 9/2009 | Ross, III et al. |
| 2015/0297808 A1 | 10/2015 | Anderson et al. |

OTHER PUBLICATIONS

Blue Sky Medical, 1 page (Publicly known at least as early as Jun. 12, 2007).

The V.A.C.® ATS® System, *KCI Licensing, Inc.*, 3 pages (Publicly known at least as early as Jun. 12, 2007).

The V.A.C.® Freedom® System, *KCI Licensing, Inc.*, 3 pages (Publicly known at least as early as Jun. 12, 2007).

V.A.C.® Canisters, *KCI Licensing, Inc.*, 4 pages (Copyright 1998-2006).

"KCI Introduces New Vacuum Assisted Closure™ Product; V.A.C.® Freedom™ Device Continues Company's Leadership in Advanced Wound Healing Systems," *PR Newswire* (Oct. 2002).

V.A.C. ® Freedom™ System Product information, www.kcil.com.

Flock Persson M. et al., "Antiseptic Wound Ventilation With a Gas Diffuser: A New Intraoperative Method to Prevent Surgical Wound Infection," Dept. of Cardiothoracic Surgery and Anesthesiology, Karolinka Institute, Huddinge University Hospital, SE-14186, Stockholm, Sweden, Aug. 2003.

\* cited by examiner

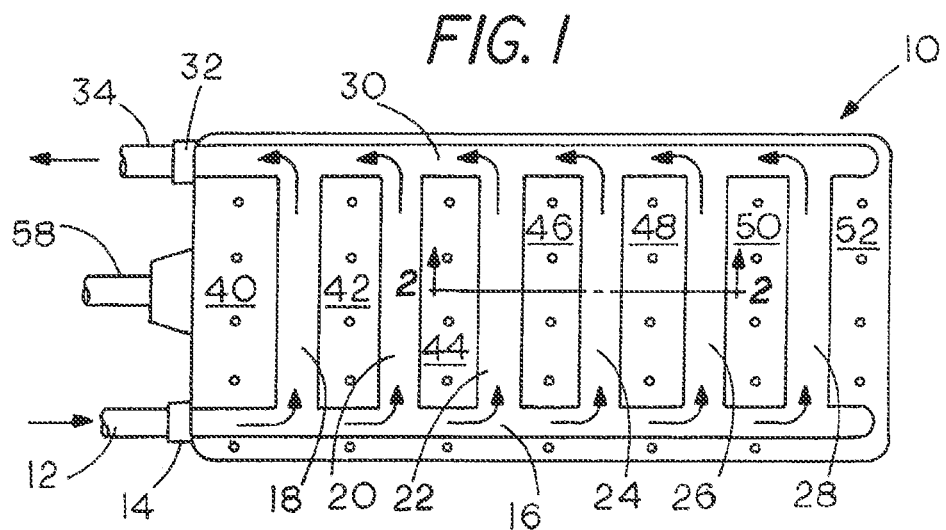
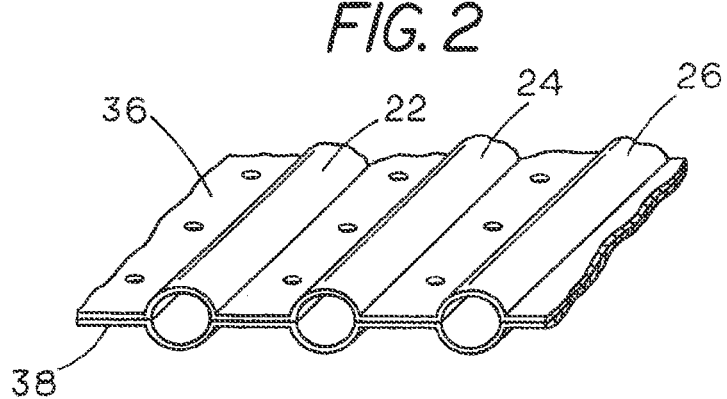
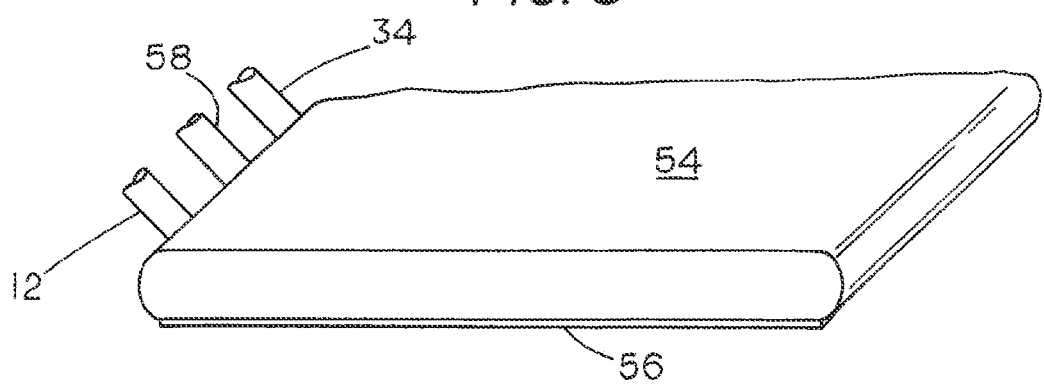

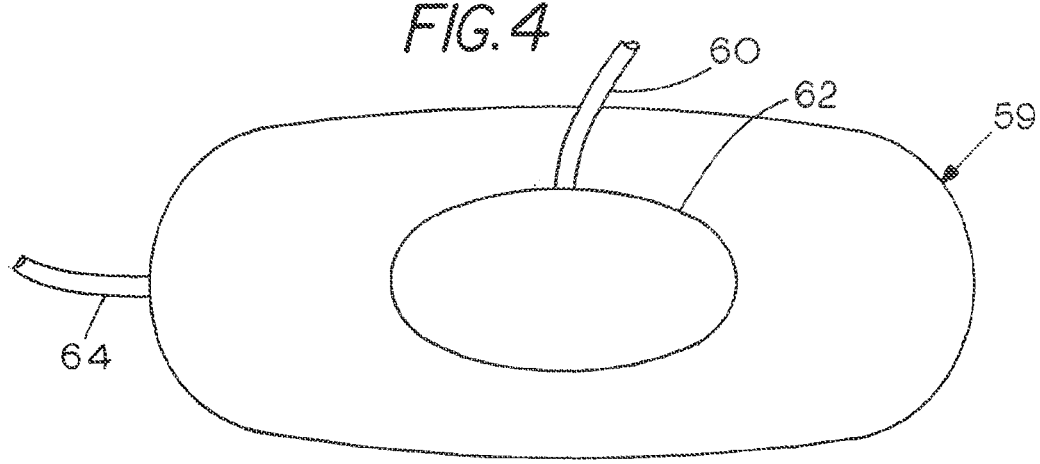
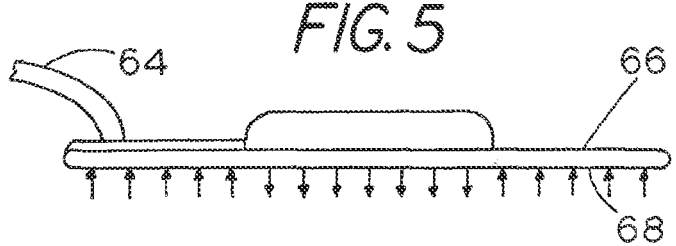
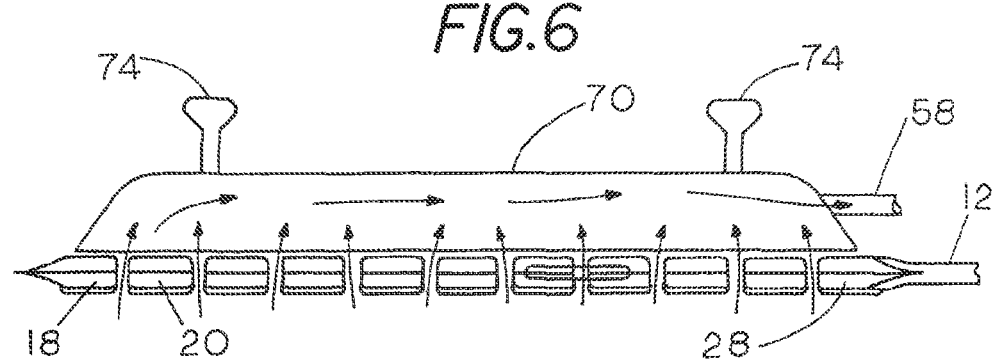
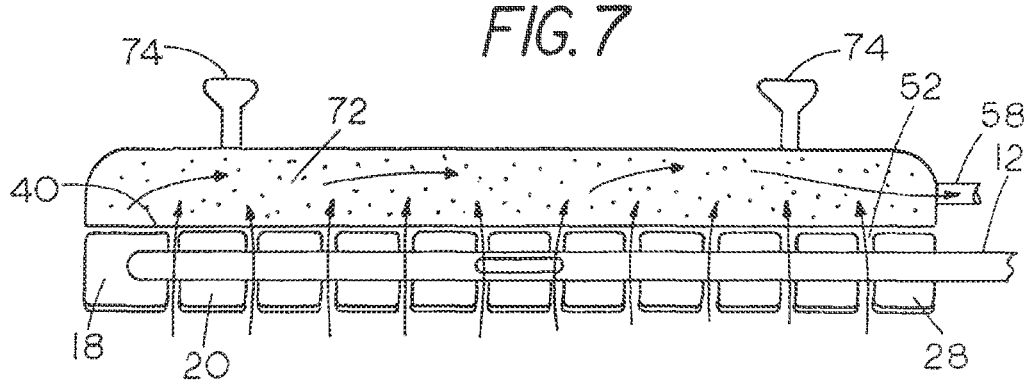

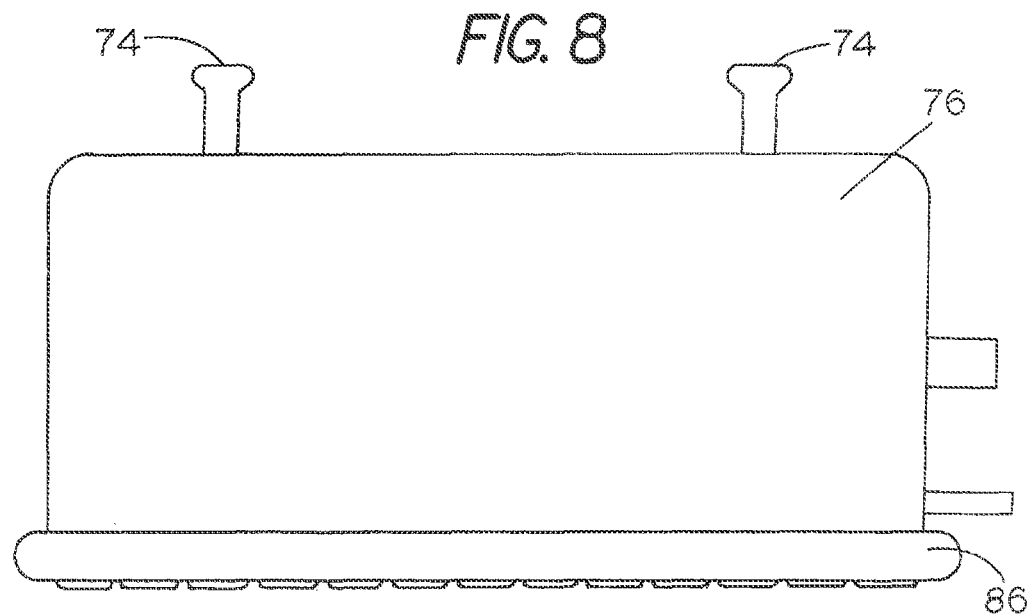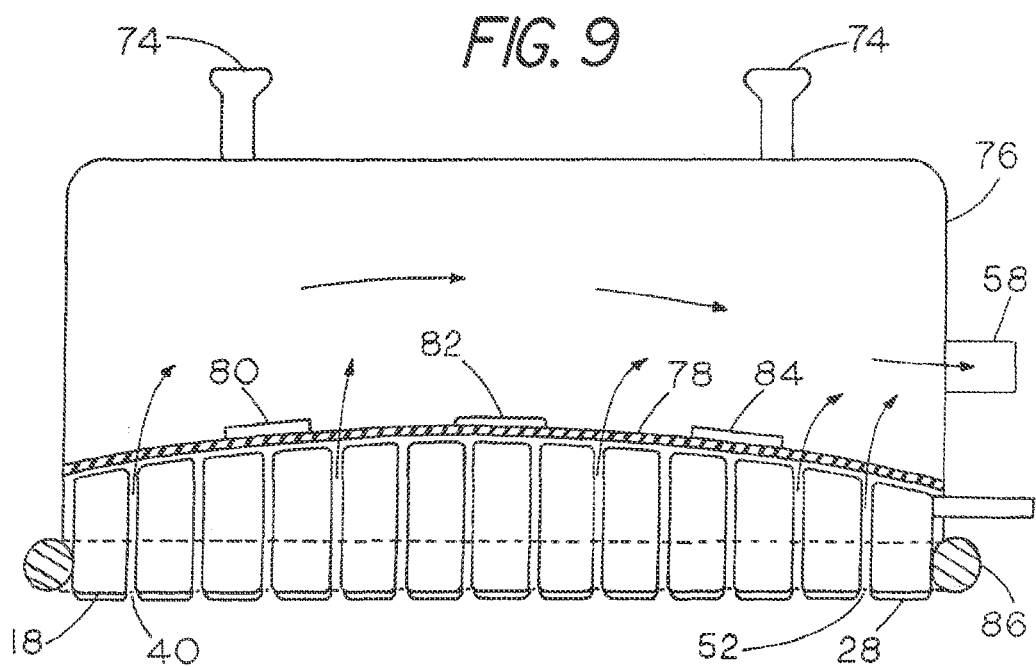

THERAPEUTIC TREATMENT PAD

CROSS-REFERENCE TO RELATED APPLICATION

This application is a divisional of application Ser. No. 13/010,254, filed Jan. 20, 2011, now U.S. Pat. No. 9,050,175, which application is incorporated herein by reference in its entirety.

BACKGROUND OF THE INVENTION

I. Field of the Invention:

This invention relates generally to a therapeutic treatment pad for applying heat, cooling or a treatment fluid to a portion of the anatomy of a subject, and more particularly to a therapeutic pad that is adhered to the body by application of a vacuum.

II. Discussion of the Prior Art:

It is well-known in the art that in treating sprains, muscle strains, skin infections and other conditions, either heat or cooling be applied to the localized area of the injury. In this regard, hot water bottles, ice bags, electrical heating pads and the like have been used. One problem that has persisted in using such devices is the fact that they are difficult to maintain in intimate contact with a patient's body where sharp contours and flexing are involved. For example, in treating a sprained ankle, applying ice to the injury counteracts the increased blood flow to the injured area and thereby reduces swelling, redness and warmth. By applying such cooling after the injury, much of the inflammation is prevented from developing. However, it is somewhat difficult to make an ice bag conform to the contour of the ankle.

Many episodes of pain come from muscle exertion or strain, which causes tension in the muscles and soft tissues. This tension can constrict circulation, sending pain signals to the brain. Heat application eases pain by dilating the blood vessels surrounding the painful area. Increased blood flow provides additional oxygen and nutrients to help heal the damaged muscle tissue. The heat application also provides a stimulating sensation in the skin, decreasing the pain signals being transmitted to the brain.

For the most part, heating pads and ice packs employ a flexible material as the housing for a heat transfer medium to thereby allow the bag or pad to be wrapped about a body part. Users have employed elastic bands and straps of one kind or another in an attempt to hold the heating/cooling pad in place at the site of the pain. Such an approach at securing the patient treatment pad or bag in place has not been altogether successful due to the presence of gaps between the surface of the treatment pad and the patient's skin. Air tends to be a good thermal barrier and, hence, the presence of an air gap between the treatment pad and the surface of the subject's skin detract from the efficacy of the treatment.

In addressing wound sepsis, it has been found that various gaseous anti-bacterial agents, when appropriately applied are effective in alleviating infections.

A need therefore exists for a therapeutic treatment pad that can readily be adhered to the body of a patient in such a way that a heat transfer surface or a gaseious medicament delivery pad remains in intimate contact with the patient's skin. The present invention fulfills such a need.

SUMMARY OF THE INVENTION

In accordance with the present invention, there is provided a therapeutic pad for use in applying heat or cooling to a body surface of a patient that comprises a generally flat, flexible housing comprising first and second major surfaces joined to one another about peripheral edges thereof, the first major surface being air impermeable and the second major surface being air permeable over at least a predetermined area thereof. Contained within the housing is a heat transfer member. Means are provided for creating a vacuum within the housing whereby a suction force is established between the second major surface of the housing for adhering it to the body surface of a patient.

The heat transfer member may take any one of a number of forms. For example, it may comprise an electric resistance wire arranged in a serpentine pattern within the housing proximate the second major surface or, alternatively, may comprise heat transmissive tubing through which either hot or chilled fluid may be made to flow. It is also contemplated that the heat transfer member may consist of a gel material that can be either heated in a microwave oven or chilled in the freezer compartment of a refrigerator, depending on the type of injury to be treated.

As a further feature of the invention, the housing may be partitioned into separate compartments whereby a vacuum can be applied over a first area of the second major surface while air under pressure is applied to a second area of the second major surface.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which:

FIG. 1 is a plan view of a first embodiment of the invention;

FIG. 2 is a cross section taken along line 2-2 in FIG. 1;

FIG. 3 is a partial view of a pad envelope in which the apparatus of FIG. 1 may be contained;

FIG. 4 is a top plan view of a second embodiment of the invention;

FIG. 5 is a side or edge view of the embodiment of FIG. 4;

FIG. 6 is a side view of a third embodiment of the invention;

FIG. 7 is a cross-sectioned view of the embodiment of FIG. 6;

FIG. 8 is a side view of a fourth embodiment of the invention;

FIG. 9 is a cross-sectional view of the embodiment of FIG. 8;

DETAILED DESCRIPTION OF THE INVENTION

Figure 10:
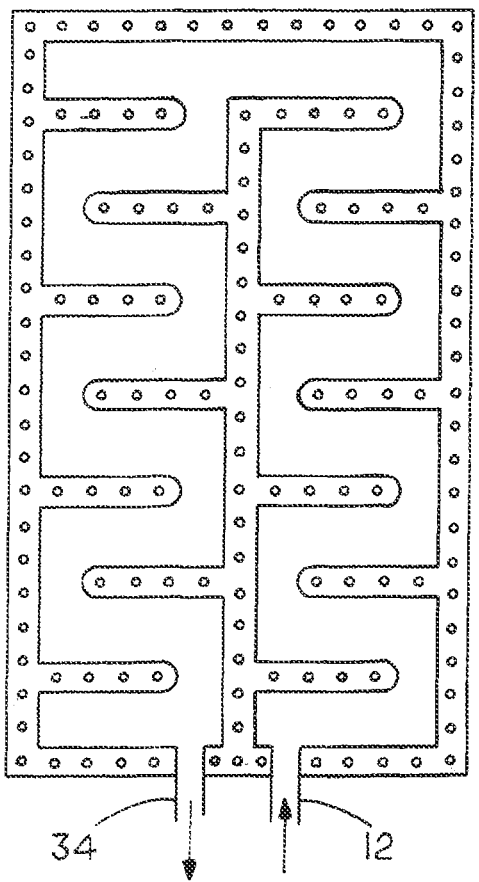
FIG. 10 is a plan view of a heating/cooling pad interior construction showing a possible heating/cooling fluid flow path.

A preferred embodiment of the present invention will now be described with reference to the accompanying drawings.

Referring first to FIGS. 1-3, there is illustrated the constructional features of a thermal treatment pad comprising a first embodiment of the invention. FIGS. 1 and 2 illustrate how two layers of a suitable thermoplastic material can be thermally bonded to one another to form a plurality of tubes through which a hot or cold fluid, either a liquid or a gas, can be made to flow.

In FIG. 1, the thermal treatment pad insert 10 serves as a heat transfer member and is seen to comprise a fluid input tube 12 connected through a seal 14 to a tubular manifold 16 that connects a plurality of tubular shunt paths 18-28 to a fluid outflow tube 30 that is coupled through a seal 32 to an external outflow tube 34.

As can be seen in FIG. 2, the shunt tubes are created by laminating two thermoplastic sheets 36-38 to one another selectively so as to create the tubular shunt paths. In the embodiment of FIGS. 1-3, the tubular shunt paths 18-28 extend parallel to one another with spaces therebetween defined by bonded segments 40, 42, 44, 46, 48 and 50.

While the thermoplastic material employed is itself impervious to fluid flow, the bonded segments 40-52 include a plurality of pinhole perforations through the thickness dimension of the joined layers 36 and 38. The insert 10 may be made in a number of sizes from, say 25 sq. in. to 6 sq. ft. and need not necessarily be rectangular in shape.

Referring next to FIG. 3, it comprises a partial view of a thermal treatment pad envelope in which the heat transfer member illustrated in FIG. 1 may be contained. It comprises a flexible, fluid impervious upper covering portion 54 and a lower porous fabric layer 56. Without limitation, the porous layer 56 may comprise any one of a variety of thermally conductive polyester filtration materials that are commercially available from a number of sources and may be thermally or adhesively bonded to the upper cover layer 54. The envelope is sized to accommodate the size of the thermal treatment pad insert 10.

In use as a heating pad, a source of heated fluid is connected to the fluid input tube 12 and the external outflow tube 34 is used to return the fluid either back to a heat source in the case of a liquid or merely exhausted to the atmosphere in the case of a heated gaseous media. At the same time, the tube 58 is connected to a vacuum source creating a negative pressure within the envelope defined by the impervious upper cover 54 and the lower pervious fabric layer 56 and thereby drawing ambient air through the porous layer 56 and the pinhole apertures formed through the joined segments 40-52. This vacuum is sufficient to closely adhere the thermal treatment pad insert 10 to an area of a subject's body to be treated, thus obviating a need for body or limb encircling straps of any kind. This intimate contact insures improved thermal transfer through the layer 56.

FIGS. 4 and 5 illustrate an alternative embodiment of the present invention. In this arrangement, heated or cooled air is directed to a selected zone of the soft, flexible pad while suction forces are developed in a remaining area of the pad to hold it in place. More particularly, heated or cooled air or an alternative gaseous media is pumped through a tubular member 60 into a pocket 62 of the thermal treatment pad while the tube 64 is connected to a vacuum source to thereby create a negative pressure within the pad in the area surrounding the pocket 62.

As can be seen in FIG. 5, the pad comprises a fluid impervious upper layer 66 and a fluid pervious or porous bottom layer 68 that may be joined together in a thermal bonding process about the periphery of the pad assembly 59 and also about the periphery of the pocket 62. Thus, two separate chambers are formed. The first chamber comprises the pocket 62 and the second chamber comprises the area surrounding this pocket. A heated or cooled fluid entering the pocket 62, via the tubular member 60, will exude out through the porous bottom layer 68 in the area of the pocket 62 while ambient air will be drawn through the perforations in the bottom layer 68 in the area surrounding the pocket 62 to cause the thermal treatment pad 59 to adhere to a patient's body at a treatment site. Layers 66 and 68 are preferably formed from a non-allergenic thermoplastic such as polyethylene, polyurethane or silicone rubber. However, other flexible thermoplastics may be used as well and limitation to polyethylene or polyurethane is not to be inferred.

The embodiment of FIG. 5 lends itself to another application. The device of FIG. 5 enables ventilation of a wound with an antiseptic agent, which in gaseous form, can be delivered as a low uniform dose to all parts of the wound. It has been found that the use of carbon dioxide ($CO_2$) as a carrier gas eliminates possible inflammability of an antiseptic agent and helps to concentrate it to the site of interest. Using the embodiment of FIG. 5 as a delivery system, the antibacterial effect of gaseous ethanol on Staphylococcus Aurous can be achieved. It has been found that ethanol is a very potent antiseptic agent with known properties, which makes it suitable for killing bacteria. The application of vacuum to the area surrounding the pocket 62 serves to effectively seal the pad to the patient's body with the pocket 62 overlaying a wound area. The application of a mixture of gaseous $CO_2$ and ethanol serves to directly apply the antibacterial fluid to the wound.

FIGS. 6 and 7 illustrate a modification to the thermal treatment pad of FIGS. 1-3 where, instead of being encased in an envelope style housing like shown in FIG. 3, the heat transfer member 10 of FIG. 1 is attached to the bottom of a filter housing 70 in which is contained a filter media 72 (FIG. 7). In this arrangement, the tube 58 leading to a vacuum source connects into the housing 70 at a location superior to the heat transfer member 10. One or more removable clips may be used to secure the sealed perimeter of the thermal treatment pad insert 10 to the perimeter of the filter housing 70 so that the two can be separated when it is desired to change the filter media 72. The filter media 72 may be a coarse, open-cell polyester or polyurethane foam, like that commonly used as air filtration media. Air can pass through it while filtering out any impurities. The filter media is selected so the application of a vacuum to the filter housing 70 prevents it from collapsing against the pinhole apertures formed in the thermal treatment pad insert 10 as earlier explained. The filter material selected and the quantity thereof contained within the housing 70 is such as to allow the resulting pad to remain quite flexible so as to be able to conform to a body contour where heating or cooling is to be applied. The plural arrows shown in FIGS. 6 and 7 illustrate the direction of airflow through the device when the tube 58 is connected to a vacuum source. If desired, handles, as at 74, may be provided on the device to facilitate placement of the thermal treatment pad on a selected body surface.

Turning next to FIGS. 8 and 9, a further embodiment of the invention is disclosed. Here, a thermal treatment pad insert 10 like that shown in FIG. 1 is attached to the base of a hard or rigid shell 76, with provision being made for the removable attachment of the thermal transfer pad insert to the base thereof. It is intended that the embodiment of FIGS. 8 and 9 be used in a massage mode. The shell 76 may be molded from a number of thermal setting plastics and, as shown in FIG. 9, an elastomeric diaphragm 78, with perforations formed therethrough is made to span the length and width dimensions of the interior of the shell 76. Ultrasonic transducers 80, 82 and 84 are affixed to diaphragm 78. The fluid carrying tubes, i.e., shunt paths 18-28 are designed to vary in height across the length dimension of the shell 76. A foam seal member 86 surrounds the base of the shell. Again, handles as at 74 are provided to allow the user to manipulate (rub) the assembly over an affected body area as heated or cooled fluid is circulated through the tubes 18-28 of the soft thermal pad and a vacuum is applied to the tube 58 drawing ambient air through the apertures in the spaces 40-52 to thereby draw the massage device into intimate contact with the subject's skin with heating or cooling being applied simultaneously with the application of soothing ultrasonic vibrations produced by the transducers 80-84. In accordance with the invention, the space in the shell 76 above the diaphragm 78 may contain a filter media as in the embodiment of FIGS. 6 and 7.

FIG. 10 is a plan view of a heat transfer pad for implementing a thermal treatment pad insert in accordance with the present invention. It is seen to comprise a serpentine fluid flow path having a fluid input tube 12 and an external outflow tube 34. Again, the pad of FIG. 10 is preferably formed using first and second sheets of a suitable thermoplastic, such as polyurethane, polyethylene, a vinyl or silicone rubber that are suitably bonded together in those areas in which are seen the pinhole apertures in FIG. 10. The areas of the two layers that are sealed together are in an interdigitated configuration to create the serpentine fluid flow path. When the thermal treatment pad of FIG. 10 is affixed to a bottom or base of a flexible or rigid cover member as in the previously described embodiments, a vacuum may be drawn causing the thermal treatment pad to adhere to a skin surface of a subject while heating or cooling fluid, introduced through the fluid input tube 12, will travel the serpentine path defined by the interdigitated fingers before exiting the external outflow tube 34 thus more directly applying the heating/cooling temperatures to the subject's skin.

Those skilled in the art can appreciate that rather than flowing a fluid through the tubular shunt paths, those paths may be filled with a heat transfer gel of the type that remains in gel form when subjected to low temperatures as when placed in a refrigerated compartment and when subjected to high temperatures when treated in a microwave oven.

Without limitation, when used in a cooling mode, the fluid may be chilled to as low as −2° Celsius and when operating in a heating mode, the fluid may typically reach a temperature of up to 43° Celsius.

Figure 11:
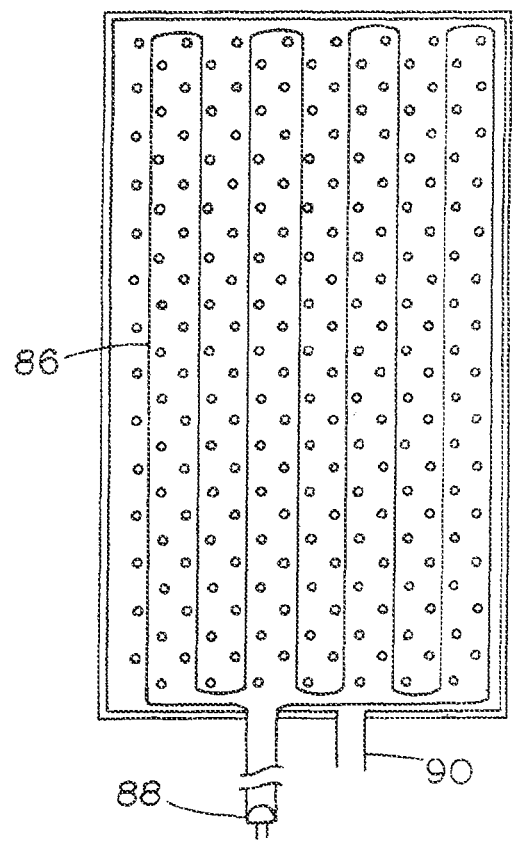
FIG. 11 shows a plan view of a heating pad interior construction with an electrical resistance wire heating element.

As seen in FIG. 11, rather than employing a heating fluid or gel, the present invention may also be implemented using an electrical resistance wire 86 sandwiched between first and second layers of flexible plastic sheets that are sealed to one another about the periphery of the pad as the heat transfer member. The bottommost layer is air pervious, either by the choice of materials employed or by providing pinhole apertures therethrough in the manner already explained. The resistance wire 86 is routed in a serpentine manner to effective cover the area of the heat transfer pad before being brought out to an electrical plug 88. Not shown in FIG. 11 but included would be a conventional thermostat control whereby the temperature can be adjustably set. Again, by connecting the tube 90 to a vacuum source, the thermal treatment pad of FIG. 11 will be drawn against a subject's skin surface insuring a more uniform heating of the skin surface subtended by the pad.

Figure 12:
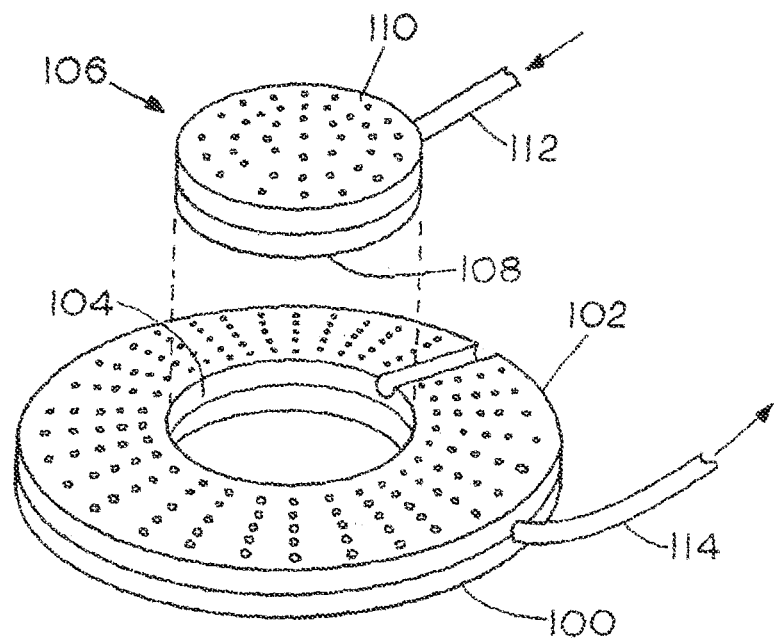
FIG. 12 is a bottom exploded perspective view of a further embodiment of a wound dressing where a vacuum is used to adhere the dressing to a subject's body.
Figure 13:
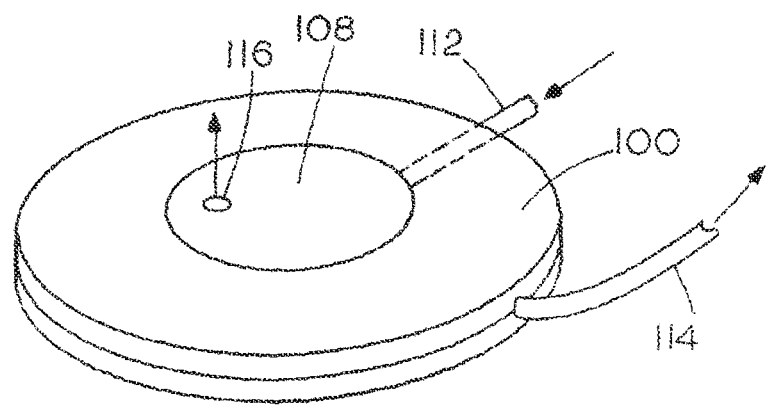
FIG. 13 is a top perspective of the embodiment of FIG. 12.

FIGS. 12 and 13 show an alternative construction of a treatment pad constructed in accordance with the present invention. In FIG. 12, a fluid impervious plastic sheet 100 is bonded about its periphery to a fluid pervious plastic sheet 102 as signified by the pinhole perforations illustrated thereon. The layer 102 has a central opening 104 and fitted therein is an insert member indicated generally numeral 106. It, too, comprises a fluid impervious plastic sheet member 108 bonded about its periphery to a perforated sheet 110. A fluid inlet tube 112 leads to the space between the sheets 108 and 110. In a similar fashion, a tube 114 leads to a volume or space between the bonded sheets 100 and 102. The insert 106 is dimensioned to fit snugly within the central opening 104.

In use, a vacuum source is connected to the tube 114 to adhere the device to a patient's body at the site of a wound while a gaseous mixture, such as $CO_2$ and ethanol is applied under pressure to the tube 112 resulting in the flow of the mixture through the perforate layer 110 overlaying the wound site.

As shown in FIG. 13, it may prove expedient to include a vent hole as at 116 in the otherwise impervious layer 108 to relieve the pressure buildup within the insert member 106. It is contemplated that faster recovery times will result when desired medical gases are delivered to a wound site with the accuracy that can be achieved with the vacuum therapy pad of the present invention.

It can be seen then that the present invention provides for the application of a vacuum to a thermal pad/wound dressing to maintain it in a desired location on a patient's body surface without the need for straps, messy adhesives or the like to hold it in place. At the same time, a fluid under pressure can be made to flow through the interior of the pad for the purpose of warming or chilling the selected treatment site or to apply a medicament in a gaseous form to the site of a wound for inhibiting infection.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, in terms of size, shape and materials used as the equipment and operating procedures, can be accomplished without departing from the scope of the invention itself.

What is claimed is:

1. A therapeutic pad for use in applying heat or cooling to a body surface of a patient comprising:
    (a) a housing comprising first and second major surfaces joined to one another about peripheral edges thereof to form an envelope, the first major surface being gas impermeable and the second major surface being gas permeable over at least a predetermined area thereof;
    (b) a treatment pad insert disposed within an interior volume of the housing and forming a temperature transfer member including a temperature conduit path defining first and second portions adjacent outer edges of the treatment pad insert with a plurality of evenly spaced intermediate portions extending across the treatment pad insert between the first and second portions adjacent the outer edges, wherein the treatment pad insert further includes a plurality of segments, each of which is interposed between and separates the intermediate portions of the temperature conduit path that extend across the treatment pad insert, each of the plurality of segments including a plurality of perforations; and (c) a vacuum tube attached to the housing and communicative with the plurality of segments, the vacuum tube configured for attachment to a vacuum source for creating a negative pressure within the interior volume of the housing for adhering the second major surface of the housing to the body surface of the patient via the plurality of perforations without the use of adhesive when the vacuum source is in operation, wherein the temperature transfer member comprises a heat transfer member coupled to an electric resistance wire within the housing and disposed proximate to the second major surface.

2. The therapeutic pad as in claim 1 wherein said housing comprises a generally rigid, fluid impervious first major surface.

3. The therapeutic pad as in claim 2 wherein the second major surface of the housing comprises a body compatible open cell foam material.

4. The therapeutic pad as in claim 1 and further including filter media contained within the housing.

5. The therapeutic pad as in claim 1 wherein the housing is sufficiently flexible so as to be made to conform to a convex contour of said body surface.

6. The therapeutic pad as in claim 1 further comprising a means for delivering an antibacterial gas through the gas permeable predetermined area of the second major surface.

* * * * *